US00PP23861P3

(12) United States Plant Patent
Benardella

(10) Patent No.: US PP23,861 P3
(45) Date of Patent: Sep. 3, 2013

(54) MINIFLORA ROSE PLANT NAMED 'BENRED'

(50) Latin Name: *Rosa hybrida*
Varietal Denomination: BENred

(75) Inventors: Frank Benardella, Millstone Township, NJ (US); June E. Benardella, legal representative, Millstone Township, NJ (US)

(73) Assignee: Greenheart Farms, Inc., Arroyo Grande, CA (US)

( * ) Notice: Subject to any disclaimer, the term of this patent is extended or adjusted under 35 U.S.C. 154(b) by 25 days.

(21) Appl. No.: 13/199,433

(22) Filed: Aug. 30, 2011

(65) Prior Publication Data

US 2013/0055474 P1 Feb. 28, 2013

(51) Int. Cl.
*A01H 5/00* (2006.01)

(52) U.S. Cl.
USPC ..... Plt./129

(58) Field of Classification Search
USPC ..... Plt./122, 150, 151, 129, 116, 143, Plt./141
See application file for complete search history.

*Primary Examiner* — Kent L Bell

(57) ABSTRACT

'BENred' is a new and distinct variety of rose plant of the miniflora class. It grows 22 to 36 inches tall and 22 to 30 inches wide, bearing dark red flowers in proportion to the size of the foliage. Blooms are borne primarily singly, last well on the plant, and are good as cut flowers. The dark green, glossy foliage offers outstanding resistance to powdery mildew.

1 Drawing Sheet

Genus and species: *Rosa hybrida.*
Varietal denomination: 'BENred'.

CROSS REFERENCE

This new rose plant bears some resemblance to 'BENnovecientos' (trade name of Power Point, not patented) and 'BENdiez' (U.S. Plant Pat. No. 17,590), two roses developed in this same breeding program from the same parentage. All plants are of an upright habit with red flowers borne primarily singly. 'BENdiez' is a miniature rose of smaller plant habit and flowers. 'BENnovecientos' is a miniflora rose of similar plant habit to the new rose but with somewhat smaller flowers. Differences immediately visible distinguishing the new rose plant from these other two rose plants are the shades of red in the open blooms of this new invention are unique, and this new rose has glossier foliage. A closer look shows the individual petals of the new invention have a broader form than those of the other two roses.

BACKGROUND OF THE INVENTION

The present plant relates to a new and distinct variety of hardy, bush type rose plant of the miniflora class. This new variety is a single seedling developed by Frank A. Benardella under controlled conditions in a greenhouse in Millstone Township (formerly Englishtown), N.J. by crossing the following two rose plants:

The seed parent is a dark red miniature rose, 'BENmjul' (U.S. patent application Ser. No. 10/035,940, filed Dec. 21, 2001, abandoned).

The pollen parent is a red hybrid tea, 'JACecond' (U.S. Plant Pat. No. 1,139).

The Primary Goal of this breeding program was to produce unique roses with award winning, hybrid tea form on plants with appealing attributes to increase public appeal. To achieve this goal roses were selected primarily for their award winning, hybrid tea form flowers and secondly for their sturdy, vigorous and attractive plant habits. Pertaining to this particular cross, both parents have been noted for their exhibition form flowers of good substance and borne one to a stem. Both parent plants are vigorous and upright growing. The seed parent has semi-glossy foliage and the pollen parent has glossy foliage. The new invention has hybrid tea form blooms of good substance, and glossy foliage on an upright plant with vigorous growth.

SUMMARY OF THE INVENTION

The present invention relates to a new and distinct variety of vigorous, hardy, bush-type rose plant of the miniflora class with dark red, hybrid tea form flowers. The field of comparison with other dark red roses is greatly reduced when the dark green glossy foliage is taken into consideration and combined with open bloom size, petal count, petal texture and appearance, and plant and foliage size.

This current plant may be characterized by

Dark red flowers, with a unique mix of dark shades of red;
A slow and gradual fade to medium shades of red.
Long lasting as a cut flower;
Flowers having hybrid tea form, primarily borne singly;
Very slight, sweet fragrance;
Dark green glossy foliage;
Excellent resistance to powdery mildew;
Upright, rounded plant habit;
Suitability for production from softwood cuttings in pots.

The present plant is compared with its parents in Table 1.

TABLE 1

| | Seed Parent, 'BENmjul' | Current Plant, 'BENred' | Pollen Parent, 'JACecond' |
|---|---|---|---|
| Flower color | Dark Red | Dark Red | Medium Bright Red (Classified as Deep Pink) |
| Petal Count | 21 to 27 | 13 to 26 | 17 to 30 |
| Foliage | Semi-glossy | Glossy | Glossy |
| Plant Size | 24" to 30" tall; 15" wide | 22" to 36" tall; 22" to 30" wide | 5' tall and 4' wide in the first year |
| Fragrance | Slight Spicy | Very Slight, Sweet | Slight |

The present invention is compared with two introduced roses, 'BENdiez' and 'BENnovecientos', developed from crossing the same parents of 'BENmjul' and 'JACecond', in Table 2.

TABLE 2

| | 'BENdiez' | Current Plant, 'BENred' | 'BENnovecientos' |
|---|---|---|---|
| Flower color | Dark Red | Dark Red | Medium, Bright Red |
| Flower diameter at exhibition stage | 1-1¾ inches | 2½-2⅞ inches | 2-2½ inches |
| Petal Count | 18-29, plus 2 to 8 or more petaloids | 13-26, most often 15-18, plus about 5 petaloids | 40-45 plus an undetermined number of petaloids |
| Foliage | Semi-glossy | Glossy | Semi-glossy |
| Plant Size | 24" to 30" tall; 15" wide | 22" to 36" tall; 22" to 30" wide | 30" to 36" tall; up to 36" wide |
| Flower Fragrance | Moderate Raspberry | Very Slight, Sweet | Slight Sweet |

BRIEF DESCRIPTION OF THE DRAWING

The accompanying illustration consists of three separate images.

Image #1 includes the four young plants used to write the description that follows. They are positioned in a way (one plant is set at a lower level than the other three) to show parts that may be considered significant identifiers: an unopened bud; a newly opened bud; a full open bloom; sepals attached to a receptacle with petals and stamens removed, exposing the pistils; and stems showing prickles and foliage. These plants are 1½ to 2 years old, growing in 5- and 6-inch pots in outdoor conditions in Ipswich, Mass.

Image #2 shows a single flowering stem, grown in a one-gallon container in a greenhouse in Arroyo Grande, Calif.

Image #3 is a bouquet of flowers in different degrees of openness, from the California grown plants. Color is depicted as nearly correct as is possible to make in a color illustration of this character.

BOTANICAL DESCRIPTION OF THE PLANT

Following is a detailed description in outline form, pertaining specifically to this new and distinct variety of rose plant as observed on plants less than 2 years old in outside conditions in Ipswich, Mass. All major color plate identifications made are referring to The Royal Horticultural Society Colour Chart except where common terms of color definition are employed.

FLOWERS

Blooming habit: Cyclic, repeating about every four weeks, though the quantity of blooms and its long bloom cycle may make it appear continuous.

Borne: Most often singly, occasionally having one or two side buds forming along the same peduncle near below the opening flower. On occasion the plant will put up a large spray of five to eight flowers.

Bud: Form is ovate with an acute apex, with the base tapering to the receptacle.

*Size.*—Length has been measured as short as 19/32 inch and as long as 30/32 inch. Width has been measured as small as 14/32 inch and as much as 19/32 inch, with width being directly related to length.

*Color when sepals first divide.*—Color is a very dark red, near 187C from the Greyed-Purple Group. The next color to show is a bit lighter, near 46A, a Currant Red.

Bloom:

*Size.*—Fully expanded, widths were 2 30/32 to 3 14/16 inches. Flower depths varied from 1 4/32 inches to 1 23/32 inches. At exhibition stage, diameters were measured 2 16/32 to 2 28/32 inches with a depth of 1 15/32 to 1 16/32 inches.

Form: The flower first opens with a high center that quickly becomes flattened convex; the lower profile begins cupped and becomes flattened convex.

Lasting quality: From when the sepals are first down until the colors began to fade was 6 to 7 days on the plant with day temperatures of 80° to 87° Fahrenheit and 7 to 8 days at cooler temperatures. When buds with sepals down were cut and kept indoors with temperatures from 70° to 76°, there were 4 days until they opened to exhibition stage and 8 days to fade.

Fragrance: Very slight, sweet.

Petalage: Counted between 13 and 26 with the most common counts of 15 and 18.

Petaloids: Counted between 1 and 7 with the most common count of 5.

Petals:

*Arrangement.*—Imbricated.

*Texture.*—The upper surface is velvety; the reverse is satiny.

*Substance.*—Excellent.

*Thickness.*—Moderately thick.

*Appearance.*—The veins on the upper surface are all recessed somewhat and to the same degree. The reverse shows all veins protruding slightly.

*Form.*—On the full open flower, the outer petals are orbicular to obtuse. At exhibition stage, about half open, these same petals were orbicular. They have a very small, acute apex and a base that is broadly obcordate to obovoid. The intermediate petals are somewhat narrower, having a broad spatulate form. Inner petals are obovate to broadly obovate.

*Margins.*—Rounded, and wavy about ⅜ inch on either side of the apex on the outer petals on the full open bloom. Margins on all petals are similar, having the wavy margin on either side of the apex.

*Size outer petals.*—Length is between 1 19/32 and 1 23/32 inches, but only varying by 1/32 inch within each flower. Widths range from 1 16/32 to 1 26/32 inches and vary within each by 3/32 to 7/32 inch.

General tonality: Dark red.

Color: During the first few days: Upper surface is shades of Cardinal Red, near 53B along the outer margin, becoming a color between 53B and 53C progressing down the petal, and near 53D just above the basal area. Margins first exposed to the sun may have a deeper red flush of between 46A and 53A. The two outermost petals have an extremely small basal area of a light Chartreuse Green near 1D. The basal area of the remaining outer petals is somewhat larger and a bit darker, near 154C. The points of attachment are near 1B. The reverse of the outer petals is near 53C, including the basal area on the two outermost petals. Other basal areas are an Empire Yellow, near 11D. The points of attachment are a very light green-yellow, near 3C.

*Color.*—WHEN HALF BLOWN: The color of the outer petals becomes a bit lighter with the upper surface of between 53B and 53C with near 46A blending in from the outer margin. Basal area is near 2D, a Chartreuse Yellow, and the point of attachment is near 1C, a Chartreuse Green. The reverse is also a bit lighter, between 53D and 60A, the basal area also a bit lighter, and the point of attachment is lighter, near 154D. The inner petals become a color between 53C and 53D and 46C, and the reverse becoming near 60D.

*Color.*—WHEN FULL BLOWN: The color continues to lighten and the tonality changes, though still a dark red. The outer petals are a rose-red, between 53D and 58B, becoming a Cardinal Red, between 53C and 53B, toward the margin with some flushing of near 53A. The basal area becomes white, near 155D and the point of attachment is near 2C. The reverse is near 58A, Indian Lake, with a basal area of a light Primrose Yellow, near 4D, and point of attachment near 2D. Progressing toward the center of the flower, the general color of the petals is the same but the basal areas of the innermost petals become near 2D and on the reverse, near 11D.

*Color as the bloom ages.*—Color continues to fade gradually.

Petaloids:

*Texture.*—Often the same as the petals, though some are satiny on both the upper and lower surfaces.

*Color.*—Same as the inner petals except the basal area and point of attachment is near 160D, a dull yellow from the Greyed-Yellow Group, the same color as the adjacent filaments.

*Size.*—On full open flowers, the width of the petaloids varied from 12/32 inch to 1 21/32 inches; lengths ranged from 15/32 inch to 1 16/32 inches, not relative to width.

*Unique characteristics.*—Many were staminiferous; some were mostly stamen-like, though not attached by a filament but with a linear base less than 2/32 inch wide, and with a very small section of petal attached; others were half petals, or deeply lobed, or bifid, or two small conjoined petals. Bases may be attenuate, or linear. Outer margins, when present, may be ruffled or entire. Any of these or other forms are found within each flower and with a white band along the main vein that seemed to be randomly located.

Sepals: The sepals roll back ahead of the petals and continue rolling back to or almost to the peduncle with some continuing to cross around the peduncle and curl up around the receptacle. They remain permanently attached to the receptacle.

*Form and characteristics.*—The 2 outermost sepals are ovato-oblong with stipitate glands along the margins and with 1 or 2 narrow foliar appendages that also have a few stipitate glands along their margins. Their attenuate apices have smaller foliar appendages lending a barbed appearance. The two innermost sepals are ovato-accuminate with a very fine pubescence along their margins and no foliar appendages. The one sepal in between the inner and outer is a combination of the inner and outer, with one foliar appendage and stipitate glands along only one margin. All sepals are truncated at the base.

*Surface appearance.*—Outside surfaces are matte becoming semi-glossy at the base.

*Surface texture.*—All sepals have a very slight pubescence and a few stipitate glands near the base on the outside surface. Inside surfaces are covered with a fine pubescence.

*Size.*—Sepals extend beyond the tip of the bud by 20/32 to 28/32 inch, just before they divide. The widths of all sepals are uniform, averaging 12/32 inch. The length of the three outer sepals averages 1 13/32 inches and the length of the two innermost sepals is noticeably shorter, between 1 7/32 and 1 8/32 inches.

*Color.*—The outside surface of the two outer sepals is a medium yellow-green, between 144A and 146B, with a lighter shade of yellow-green, near 144C, in the center. The apices are glossy and a much deeper yellow-green, near 147A. The three inner sepals are near 146D along the margins and near 144C in the center. The inside surfaces of all sepals are near 147B along the margins, and a very light yellow-green, near 145C, in the center.

Peduncle:

*Aspect.*—Near straight, most often a slight curve sunward.

*Strength.*—Strong.

*Size.*—Lengths vary from 1 28/32 to 2 inches. Diameters are near uniform, averaging about 6/32 inch right below the receptacle and tapering to 4/32 inch at the juncture with the stem.

*Color.*—Light yellow-green, between 144C and 146D, lightly flushed with a dull red on the sunward side, near 181B from the Greyed-Red Group.

*Texture.*—Semi-glossy, becoming glossy near the top where it is joined to the receptacle.

*Surface.*—The entire surface is covered with many very soft prickles, measuring as short as 1/64 inch to as long as 3/32 inch. The color of the prickles is near 181A.

Receptacle:

*Color.*—A Scheele's Green, near 144B, and may have an anthocyanin flushing of a deep red, near 178A, on a side exposed directly to the sun.

*Surface.*—Glossy. There is a light covering of a very fine pubescence, though it appears glabrous to the naked eye.

*Size.*—Averaging 12/32 inch at its widest point, with an average height of 18/32 inch.

*Shape.*—Conical, tapering evenly to connect with the peduncle.

*Top surface of the receptacle.*—Has a circular shape usually with a diameter of around 10/32 inch. The color is a light yellow-green near 145D. There are short tufts of hairs that surround the pistils.

REPRODUCTIVE ORGANS

Stamens, filaments and anthers:

*Arrangement.*—Two tight rows are situated adjacent to the petals.

*Quantity.*—Between 114 and 190.

*Filaments.*—The tops gently curve toward the pistils.

*Length.*—Length varies from 9/32 to 17/32 inch in the full open flower.

*Color.*—A light red, between 47B and 50B, for the upper half, and a dull, medium yellow, between 160C and 160D from the Greyed-Yellow Group, for the lower half.

*Anthers.*—Color near 11D, Empire Yellow.

*Pollen.*—Color of pollen sacs is a dull shade of gold, near 163B from the Greyed-Orange Group.

Pistils, styles and stigmas: Originating in the alveola in the center of the top of the receptacle, and surrounded by tufts of short hairs.

*Quantity.*—Counted at 35 to 46.

*Styles.*—Moderately thin, most are very straight.

*Length.*—In the full open flower, lengths of the styles varied from 7/32 to 13/32 inch.

*Color.*—Medium red, near 45B, from right below stigma, then white, between 155D and 155B, into the alveola.

*Stigmas.*—A medium Cadmium Orange, near 23C.

Hips: There were only two hips to observe. Following is their description.

*Shape.*—Between urceolate and conical.

*Size.*—Not symmetrically round: 18/32 by 20/32 inch diameters and 25/32 inch height on a hip with no seeds protruding, and 13/32 by 14/32 inch diameters and 22/32 inch height on a hip with seeds protruding.

*Surface texture.*—Glabrous.

*Color when mature.*—The color of the mature hip, when grown under lights, was a dark orange, between 26A and 28B.

PLANT

Habit: The habit of the current plant is upright, rounded, and well branched.

Growth: Vigorous. New shoots initiate on flowering stems after sepals divide.

*Size.*—The plant grows 22 to 36 inches tall and 22 to 30 inches wide.

*Root initiation from cuttings.*—3 to 6 days under controlled, greenhouse conditions.

Stem diameter: Main canes observed had a basal diameter of 10/32 inch. Primary laterals had a basal diameter of 7/32 to 8/32 inch 7/32 to 8/32 inch, becoming 6/32 inch at the top. Flowering stems had a diameter of 5/32 to 7/32 inch at the base and tapered to 4/32 to 5/32 inch where they joined with the peduncle.

Length of flowering stems: The length of the flowering stem is determined by how far it originates from the crown of the plant. Flowering stems originating lower down on the plant have been measured from 9½ to 13½ inches long while stems originating nearer the top of the plant have been measured as short as 3½ inches.

Length of internodes: Quite variable: The spacing of the internodes seems to be greater on the longer flowering stems, varying from 1 5/32 to 1 21/32 inches, but also as short as 20/32 inch. Internodes were shortest near the base. On these longer stems there are generally 7 to 9 five-leaflet leaves, regardless of stem length. The shorter flowering stems have fewer leaves and shorter internodes of 20/32 to 33/32 inch.

Foliage: Pinately compound leaves, mostly with five leaflets but also with three or seven. Flowering stems usually have 7 to 9 five-leaflet leaves plus 1 to 3 three-leaflet leaves just below the peduncle, regardless of the length of the stem. 7-leaflet leaves, when present, are usually closest to the base of the stem.

Size of mature leaf: Mature leaves on these plants had lengths ranging from 3 24/32 inches to 4 24/32 inches. Seven-leaflet leaves tended to be longest. Lengths of the three- and five-leaflet leaves were not in relation to the number of leaflets.

Leaflets:

*Shape.*—Most are ovate, though some are just narrow-ovate, on the same plant and the same stem. Apices are acute. Bases are oval, being narrower oval on the narrow-ovate leaflets.

*Appearance.*—Upper surface is glossy. Main veins are entirely recessed and primary laterals are somewhat recessed. The reverse is matte. Main veins protrude entirely, primary lateral veins protrude mostly, and secondary lateral veins are barely protruding.

*Texture.*—Upper surface is glabrous; the reverse is somewhat leathery.

*Edge.*—Margins have a simple and near even serration, with a gland at the tip of each serrate.

*Size of terminal leaflets.*—Lengths of terminal leaflets on five- and seven-leaflet leaves were measured from 1 20/32 inches to 2 13/32 inches. Their widths were measured from 31/32 inch to 1 15/32 inches. Three leaflet leaves found on the lower portion of the plant had larger terminal leaflets, ranging from 2 10/32 to 2 27/32 inches long and 1 8/32 to 1 22/32 wide.

Color new foliage: Upper surface is a dark olive-green near 146B, heavily flushed with a deep red, between 187A and 183A. The reverse is a medium olive green, near 146B, and heavily flushed with *Chrysanthemum* Crimson, near 185B.

Color older foliage: Anthocyanin color is absent. The upper surface is a dark green, between 139A and 146A. The reverse is lighter, near 137C.

Petiole: Color on young petioles is near 187A, along the ridges and in the groove. Between the stipules the color becomes near 183B, an Oxblood Red. The reverse is lighter, near 183C, from the juncture with the basal leaflets, becoming near 146C between the stipules.

*Size.*—Petioles on three-leaflet leaves were longest, measured from 1 8/32 inches to 1 22/32 inches. Seven-leaflet leaves had the shortest petioles, measured 20/32 inch and 22/32 inch. Five-leaflet leaves had petioles from 31/32 inch to 1 4/32 inches.

*Texture/appearance.*—The ridges along the upper surface of the petiole were lined with stipitate glands, seemingly paired with those on the opposite ridge. The under surface occasionally had a single prickle.

Rachis: The colors are the same as those of the petioles.

*Size.*—Lengths of the rachis on five-leaflet leaves varied from 22/32 to 28/32 inch. Lengths of the rachis on seven-leaflet leaves averaged around 1 11/32 inches.

*Texture/appearance.*—The ridges on the upper surface had slightly fewer stipitate glands than found on the ridges of the petiole. The reverse occasionally had a single prickle, and stipitate glands clustered just below the juncture with leaflets.

Petiolules: The color of the petiolules on the mature foliage was notably lighter than that of the rachis or petioles. Along the ridges and in the grooves the color of the upper surface was a very light yellow-green, between 144D and 149C; the reverse was between 149D and 144D.

*Size.*—Petiolules to the terminal leaflets were shortest on the seven-leaflet leaves, measured at 15/32 and 16/32 inch. Petiolules to the terminal leaflet on the five-leaflet leaves were measured from 17/32 to 21/32 inch.

*Texture/appearance.*—Stipitate glands were along the ridges on the upper surface.

Stipules: 2 are paired at the base of each leaf. 2 or 3 were also located at the base of flowering stems.

*Size.*—The length of stipules attached to the petioles at the base of five- and seven-leaflet leaves varied from 10/32 inch to 16/32 inch attached and 4/32 to 5/32 inch angled outward at an angle anywhere from 7° to 45° from the petiole. The length attached usually varied by 1/32 inch within each pair. Stipules were longest on the three-leaflet leaves where they reached lengths of 19/32 inch attached and 6/32 to 7/32 inch angled outward.

*Color.*—When young the upper surface was a medium yellow green near 146B with a slight brown-red flush. The reverse was a bit lighter, near 146C, with no anthocyanin coloring. On mature leaves, the upper surface had darkened to near 137B with no anthocyanin coloring and the reverse to near 146B.

*Margins.*—Heavily lined with stipitate glands of very uneven lengths. Edges were often gently rolled back a bit.

Other foliar appendages: Two or three stipulate appendages were located at the base of the flowering stems. They were connate, being completely joined together down the center, from the base to the tips, and attached directly to the stems along their base. The color of the upper surface where they were joined together was between 145C and 154D, a pale yellow green, and flushed with near 181B. The outer edges were a much darker green, between 139A and 137A. ON flowering stems, at and just below the juncture of the peduncles were usually one or two simple leaves with stipules attached the entire length of their petioles, and/or a single or pair of stipulate appendages. A single three-leaflet leaf may be present but was never observed to be at the juncture but a bit below. Coloring of these appendages was the same as found on the adjacent foliage.

Resistance: The glossy foliage is very resistant to powdery mildew and rust but somewhat susceptible to black spot in Massachusetts.

Wood: Stems are gently curved or slightly crooked at each node.

*Texture new wood.*—Glabrous, except for prickles.

*Texture old wood.*—Lenticels seem to form in the second year of growth, starting at the base of the oldest canes.

*Color new wood.*—Medium yellow-green, near 146C and quickly becoming near 146B, with the sunward side flushed with a deep terra cotta red, between 173A and 178A.

*Color old wood.*—Medium green, between 137C and 147A. Lenticels are a medium brown, near 177B, from the Greyed-Orange Group.

Prickles:

*Quantity.*—Older canes have 8 to 10, and occasionally more, between nodes. Flowering stems had 2 to 4, usually 3 or 4, between nodes, except near the base where the quantity was about doubled.

*Length.*—Prickles located on the canes of the plant seemed to be uniformly around 1/4 inch long, except near the base of the flowering stems where lengths varied from 3/32 to 7/32 inch.

*Form.*—Angled or slight arc downward.

*Color.*—When young, prickles in full sun are near 182A, a medium color from the Greyed-Red Group. When somewhat protected from the sun they are lighter, near 182C. The tips gradually become a light brown, near 177D. When old the entire prickle becomes an olive-brown, near 199A from the Greyed-Brown Group.

Hardiness: This new rose cultivar has been tested hardy to USDA Zone 5.

The new invention claimed is:

1. A new and distinct variety of hardy rose plant of the miniflora class, substantially as illustrated and described herein, with hybrid tea form flowers of dark red, borne primarily singly, holding up well as cut flowers, and with dark green, glossy foliage on a well-branched plant.

* * * * *

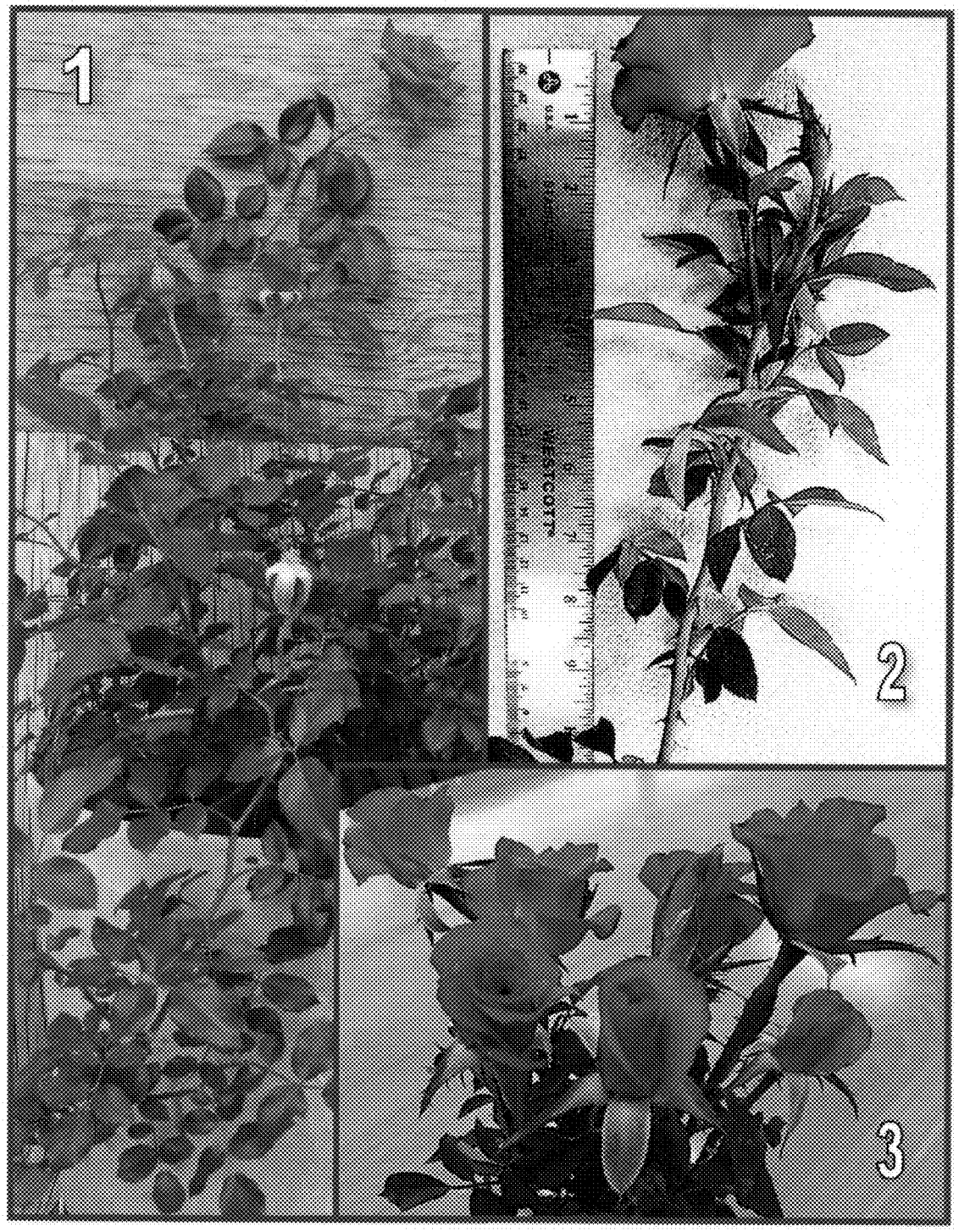
1
2
3